US 11,125,354 B2

(12) United States Patent
Carmody et al.

(10) Patent No.: US 11,125,354 B2
(45) Date of Patent: Sep. 21, 2021

(54) CHECK VALVE ASSEMBLY

(71) Applicant: Illinois Tool Works Inc., Glenview, IL (US)

(72) Inventors: Colm M. Carmody, Listowel (IE);
Gerard G. Henn, Limerick (IE);
Robert R. Schaser, Chicago, IL (US);
Raymond Jozwik, Hendersonville, TN (US); David Drake Thompson, Greenville, NC (US); Michael Grant Leonhard, West Bend, WI (US);
Brendan Casey, Ballinira (IE); Yash Siddhartha, Chicago, IL (US);
Elizabeth O Connor, Newcastle West (IE)

(73) Assignee: ILLINOIS TOOL WORKS INC., Glenview, IL (US)

(*) Notice: Subject to any disclaimer, the term of this patent is extended or adjusted under 35 U.S.C. 154(b) by 74 days.

(21) Appl. No.: 16/585,691

(22) Filed: Sep. 27, 2019

(65) Prior Publication Data

US 2020/0025308 A1 Jan. 23, 2020

Related U.S. Application Data

(63) Continuation-in-part of application No. 15/762,639, filed as application No. PCT/US2016/048839 on Aug. 26, 2016, now Pat. No. 10,682,109.

(Continued)

(51) Int. Cl.
*F16K 31/126* (2006.01)
*F16K 27/02* (2006.01)
(Continued)

(52) U.S. Cl.
CPC ......... *F16K 31/1268* (2013.01); *A61M 39/24* (2013.01); *F16K 15/023* (2013.01);
(Continued)

(58) Field of Classification Search
CPC ............ Y10T 137/7838; A61M 39/24; A61M 2039/2433; F16K 15/023; F16K 31/1268; F16K 27/0236
See application file for complete search history.

(56) References Cited

U.S. PATENT DOCUMENTS 3,297,048 A ‡ 1/1967 Imhof .................. B60T 11/323
137/512
3,586,038 A * 6/1971 Jahrstorfer ............. F16K 15/03
137/512

(Continued)

FOREIGN PATENT DOCUMENTS

WO     WO 93/01859-    ‡   2/1993
WO     WO 2014/140158-   ‡   9/2014
WO     2017062110 A1    4/2017

OTHER PUBLICATIONS

International Search Report and Written Opinion for PCT/US2016/048839.‡

(Continued)

*Primary Examiner* — Marina A Tietjen
*Assistant Examiner* — Frederick D Soski
(74) *Attorney, Agent, or Firm* — Christopher R. Carroll; The Small Patent Law Group LLC

(57) ABSTRACT

An infusion set check valve assembly includes a self-contained housing that defines inlet ports and an outlet port. The assembly also includes at least one check valve disposed within the self-contained housing between the outlet channel and at least one of the inlet ports. The at least one check valve is configured to open for a first fluid to flow from a first inlet to a patient line via an outlet channel while (Continued)

a second fluid also flows from a second inlet to the patient line via the outlet channel. The at least one check valve closes to prevent the first fluid from flowing to the patient line via the outlet channel while the second fluid flows to the patient line.

16 Claims, 7 Drawing Sheets

Related U.S. Application Data

(60) Provisional application No. 62/238,203, filed on Oct. 7, 2015.

(51) Int. Cl.
 *F16K 15/02* (2006.01)
 *A61M 39/24* (2006.01)

(52) U.S. Cl.
 CPC . *F16K 27/0236* (2013.01); *A61M 2039/2433* (2013.01); *Y10T 137/7838* (2015.04)

(56) References Cited

U.S. PATENT DOCUMENTS

| | | | | |
|---|---|---|---|---|
| 3,807,445 A ‡ | 4/1974 | McPhee | ............ | A61M 16/0051 137/557 |
| 4,222,407 A ‡ | 9/1980 | Ruschke | ............... | F16K 15/141 137/512.15 |
| 4,244,378 A ‡ | 1/1981 | Brignola | ............ | A61B 5/15003 137/843 |
| 4,246,932 A ‡ | 1/1981 | Raines | .................... | A61M 5/31 137/51 |
| 4,354,492 A ‡ | 10/1982 | McPhee | .................. | A61M 5/40 137/528 |
| 4,405,316 A | 9/1983 | Mittleman | | |
| 4,415,003 A ‡ | 11/1983 | Paradis | .................... | F16K 15/14 137/843 |
| 4,556,086 A ‡ | 12/1985 | Raines | ................. | F16K 15/141 137/843 |
| 4,762,149 A ‡ | 8/1988 | Pickl, Jr. | ............... | F16K 15/141 137/843 |
| 4,838,875 A ‡ | 6/1989 | Somor | ..................... | A61J 1/10 604/247 |
| 4,946,448 A ‡ | 8/1990 | Richmond | ............ | A61M 39/24 137/493.9 |
| 5,070,905 A ‡ | 12/1991 | Paradis | ................. | A61M 39/04 137/606 |
| 5,190,067 A ‡ | 3/1993 | Paradis | ................. | A61M 39/04 137/1 |
| 5,391,150 A ‡ | 2/1995 | Richmond | ................ | A61J 1/10 604/111 |
| 5,431,185 A | 7/1995 | Shannon et al. | | |
| 5,623,969 A ‡ | 4/1997 | Raines | .................. | A61M 39/24 137/854 |
| 5,992,462 A ‡ | 11/1999 | Atkinson | ............... | A61M 39/24 137/515.5 |
| 6,409,707 B1 ‡ | 6/2002 | Guala | .................... | A61M 39/24 137/843 |
| 6,866,056 B1 ‡ | 3/2005 | Scott | ..................... | B60K 15/035 137/15.18 |
| 6,953,453 B2 | 10/2005 | Recinella et al. | | |
| 8,162,006 B2 ‡ | 4/2012 | Guala | .................... | A61M 39/24 137/512.15 |
| 8,480,645 B1 * | 7/2013 | Choudhury | ........... | A61M 5/158 604/411 |
| 8,973,596 B2 ‡ | 3/2015 | Hull | ....................... | F16K 15/023 137/1 |
| 10,286,202 B2 ‡ | 5/2019 | Mosler | .................. | A61M 39/24 |
| 2002/0156431 A1 ‡ | 10/2002 | Feith | ................... | A61M 5/1408 604/24 |
| 2005/0121103 A1 ‡ | 6/2005 | Steigerwalt | ............. | A61J 3/002 141/10 |
| 2005/0194047 A1 | 9/2005 | Bausmith | | |
| 2006/0173420 A1 | 8/2006 | Fangrow, jr. | | |
| 2008/0172006 A1 | 7/2008 | Hicks | | |
| 2010/0300556 A1 ‡ | 12/2010 | Carmody | .............. | A61M 39/24 137/528 |
| 2016/0166761 A1 | 6/2016 | Piehl et al. | | |
| 2017/0120028 A1 | 5/2017 | Burkholz et al. | | |
| 2017/0281870 A1 ‡ | 10/2017 | Kai | .................. | A61B 17/00491 |
| 2017/0319783 A1 | 11/2017 | Piehl et al. | | |
| 2019/0093775 A1 | 3/2019 | Feith et al. | | |

OTHER PUBLICATIONS

Extended European Search Report dated Jan. 13, 2021 for corresponding EP Application No. 20197108 (13 pages).

\* cited by examiner
‡ imported from a related application

CHECK VALVE ASSEMBLY

CROSS-REFERENCE TO RELATED APPLICATIONS

This application is a continuation-in-part of U.S. patent application Ser. No. 15/762,639, filed 23 Mar. 2018, which is a national stage application of 35 U.S.C. § 371(c) of PCT application serial number PCT/US2016/048839, filed 26 Aug. 2016, which claims priority to U.S. Provisional Application No. 62/238,203, filed 7 Oct. 2015. The entire disclosures of these applications are incorporated herein by reference.

FIELD OF EMBODIMENTS OF THE DISCLOSURE

Embodiments of the present disclosure generally relate to a check valve assembly, and, more particularly, to a check valve assembly that may be configured for medical applications, such as for use with computed tomography (CT) imaging.

BACKGROUND

During certain types of medical imaging (such as during computed tomography imaging), contrast agent may be used. For example, an individual may ingest or be injected with contrast agent before the imaging process. When the individual is being imaged, the contrast agent allows for more defined imaging results.

During an imaging session, saline and contrast merge within a connection joint that connects to a syringe through a conduit. A check valve is typically positioned within each of a saline line and a contrast line. For example, the saline line includes a first check valve, and the contrast line includes a separate and distinct second check valve. The check valves are separated from the connection joint. Because the check valves are separated from the connection joint, small amounts of contrast may be drawn into the saline during a flush through the connection joint (or vice versa), which may, in turn, affect the resulting acquired images of anatomy. For example, the contrast may form spots on a scanned image, thereby creating a false positive.

BRIEF DESCRIPTION

A need exists for a check valve assembly that prevents, minimizes, or otherwise reduces the possibility of saline and contrast undesirably mixing. A need exists for a check valve assembly that prevents, minimizes, or otherwise reduces the possibility of image false positives, such as may be caused by spots formed by contrast agent. A need exists for a simpler and more effective check valve assembly.

With those needs in mind, certain embodiments of the present disclosure provide a check valve assembly that is configured to couple to a first container that retains a first fluid and a second container that retains a second fluid. The check valve assembly includes a fluid inlet housing including a first fluid inlet port defining a first fluid inlet channel, and a second fluid inlet port defining a second fluid inlet channel. A fluid outlet housing is coupled to the fluid inlet housing. The fluid outlet housing includes a fluid outlet port defining a fluid outlet channel. A first diaphragm is seated over the first fluid inlet channel. At least a portion of the first diaphragm is configured to unseat over the first fluid inlet channel to allow the first fluid to pass from the first fluid inlet channel into the fluid outlet channel. A second diaphragm is seated over the second fluid inlet channel. At least a portion of the second diaphragm is configured to unseat over the second fluid inlet channel to allow the second fluid to pass from the second fluid inlet channel into the fluid outlet channel.

In at least one embodiment, each of the first and second diaphragms includes an annular edge radially extending from a central hub. The annular edge includes an outer rim that is thicker than the central hub.

The check valve assembly may include one or more walls surrounding a fluid chamber between the first and second fluid inlet channels and the fluid outlet channel. One or more guide ribs may inwardly extend from the wall(s). The guide ribs constrain, a least in part, one or both of the first and second diaphragms. The guide ribs are configured to guide fluid flow from the first and second inlet channels toward the fluid outlet channel. In at least one embodiment, each of the guide ribs includes a stem connected to a beveled tip.

The check valve assembly may include a deflecting barrier positioned between openings of the first and second fluid inlet channels.

The check valve assembly may include a first restraining protuberance that abuts into the first diaphragm, and a second restraining protuberance that abuts into the second diaphragm.

The check valve assembly may include a first plurality of supporting protuberances that control a range of deflection of the first diaphragm. The first plurality of supporting protuberances block further deflection of the portion(s) of the first diaphragm when the portion(s) of the first diaphragm unseats over the first fluid inlet channel. A second plurality of supporting protuberances control a range of deflection of the second diaphragm. The second plurality of supporting protuberances block further deflection of the portion(s) of the second diaphragm when the portion(s) of the second diaphragm unseats over the second fluid inlet channel.

Certain embodiments of the present disclosure provide a fluid delivery system that includes a first fluid container that retains a first fluid, a second fluid container that retains a second fluid, and a check valve assembly coupled to the first container and the second container. The check valve assembly includes a fluid inlet housing including a first fluid inlet port defining a first fluid inlet channel fluidly connected to the first fluid container, and a second fluid inlet port defining a second fluid inlet channel fluidly connected to the second fluid container. A fluid outlet housing is coupled to the fluid inlet housing. The fluid outlet housing includes a fluid outlet port defining a fluid outlet channel. A first diaphragm is seated over the first fluid inlet channel. At least a portion of the first diaphragm is configured to unseat over the first fluid inlet channel to allow the first fluid to pass from the first fluid inlet channel into the fluid outlet channel. A second diaphragm is seated over the second fluid inlet channel. At least a portion of the second diaphragm is configured to unseat over the second fluid inlet channel to allow the second fluid to pass from the second fluid inlet channel into the fluid outlet channel.

The fluid delivery system may also include a syringe fluidly connected to the fluid outlet port. In at least one embodiment, the first fluid container is a contrast container, the first fluid is a contrast agent, the second fluid container is a saline container, and the second fluid is saline.

In one embodiment, an infusion set check valve assembly includes a self-contained housing that defines at least a first inlet port, a second inlet port, and a fluid outlet port. The first inlet port defines a first inlet channel through which a first fluid is received from a first container that retains the first fluid. The second inlet port defines a second inlet channel through which a second fluid is received from a second container that retains the second fluid. The outlet port defines an outlet channel through which one or more of the first fluid or the second fluid received into the self-contained housing via one or more of the first inlet port or the second inlet port is directed to a patient line. The assembly also includes at least one check valve disposed within the self-contained housing between the outlet channel and at least one of the first inlet channel or the second inlet channel. The at least one check valve is configured to open for the first fluid to flow from the first inlet channel to the patient line via the outlet channel while the second fluid also flows from the second inlet channel to the patient line via the outlet channel. The at least one check valve is configured to close to prevent the first fluid from flowing from the first inlet channel to the patient line via the outlet channel while the second fluid flows from the second inlet channel to the patient line via the outlet channel.

In one embodiment, an infusion set fluid delivery system includes a first container configured to retain a first fluid and an infusion set check valve assembly that includes a self-contained housing defining at least a first inlet port, a second inlet port, and a fluid outlet port. The first inlet port defines a first inlet channel through which the first fluid is received from the first container. The second inlet port defines a second inlet channel through which a second fluid is received from a second container that retains the second fluid. The outlet port defines an outlet channel through which one or more of the first fluid or the second fluid received into the self-contained housing via one or more of the first inlet port or the second inlet port is directed to a patient line. The infusion set check valve assembly also includes at least one check valve disposed within the self-contained housing between the outlet channel and at least one of the first inlet channel or the second inlet channel. The at least one check valve is configured to open for the first fluid to flow from the first inlet channel to the patient line via the outlet channel while the second fluid also flows from the second inlet channel to the patient line via the outlet channel. The at least one check valve is configured to close to prevent the first fluid from flowing from the first inlet channel to the patient line via the outlet channel while the second fluid flows from the second inlet channel to the patient line via the outlet channel.

In one embodiment, an infusion set check valve assembly includes a self-contained housing that defines at least a first inlet port, a second inlet port, and a fluid outlet port. The first inlet port defines a first inlet channel through which a first fluid is received from a first container that retains the first fluid. The second inlet port defines a second inlet channel through which a second fluid is received from a second container that retains the second fluid. The outlet port defines an outlet channel through which one or more of the first fluid or the second fluid received into the self-contained housing via one or more of the first inlet port or the second inlet port is directed to a patient line. The assembly also includes a first check valve located between the first inlet channel and the outlet channel and a second check valve located between the second inlet channel and the outlet channel. The first check valve is configured to open for the first fluid to flow from the first inlet channel to the patient line via the outlet channel while the second check valve opens for the second fluid to concurrently flow from the second inlet channel to the patient line via the outlet channel. The first check valve is configured to close to prevent the first fluid from flowing from the first inlet channel to the patient line via the outlet channel while the second check valve remains open for the second fluid to continue flowing from the second inlet channel to the patient line via the outlet channel.

Figure 1:
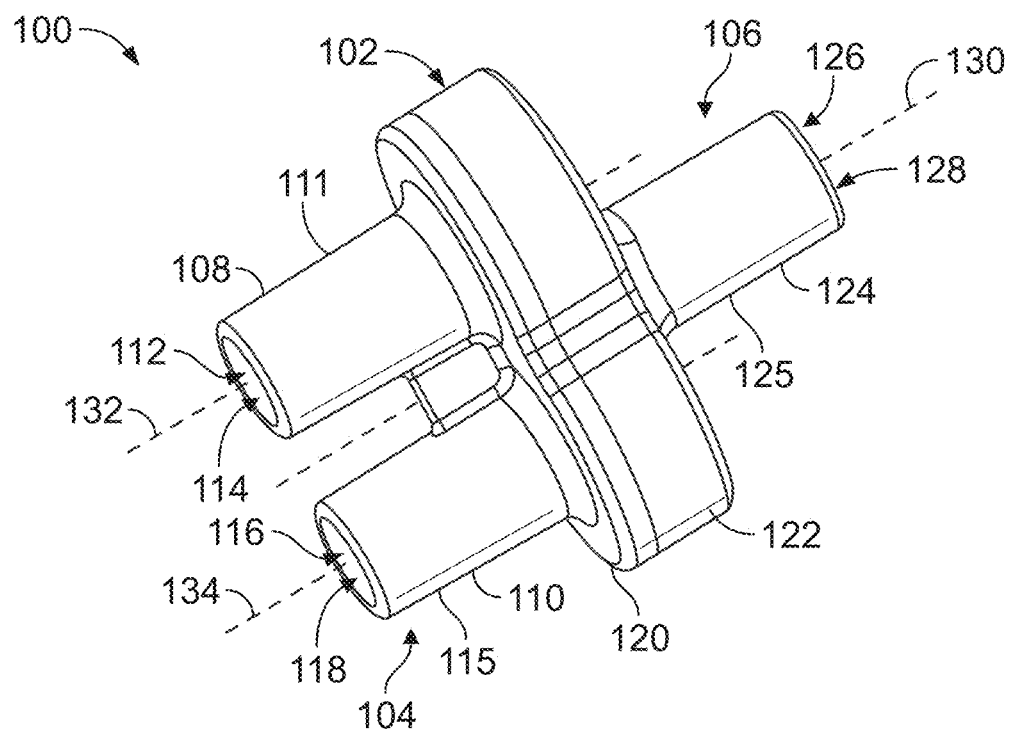
FIG. 1 illustrates a perspective view of a check valve assembly, according to an embodiment of the present disclosure.

Before the embodiments of the disclosure are explained in detail, it is to be understood that the disclosure is not limited in its application to the details of construction and the arrangement of the components set forth in the following description or illustrated in the drawings. The disclosure is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION

Embodiments of the present disclosure provide a check valve assembly that is configured to prevent undesired mixing of contrast and saline, for example, during CT imaging or other medical procedures and/or imaging. The check valve assembly reduces the likelihood of false results.

Embodiments of the present disclosure provide a check valve assembly at the point where the contrast and saline merge, thereby preventing mixing when one fluid is being injected. Embodiments of the present disclosure lead to more accurate diagnoses and save costs (such as through a simpler and more efficient system and method).

FIG. 1 illustrates a perspective view of a check valve assembly 100, according to an embodiment of the present disclosure. The check valve assembly 100 may be a dual check valve assembly that is normally closed. The check valve assembly 100 includes a main body 102 that includes a fluid inlet (or entry) portion 104 coupled to a fluid outlet (or exit) portion 106. Each of the fluid inlet housing 104 and the fluid outlet housing 106 may be formed of a plastic, for example. The fluid inlet housing 104 may be securely connected to the fluid outlet housing 106, such as through ultrasonic welding. In at least one other embodiment, the fluid inlet housing 104 may be securely connected to the fluid outlet housing 106 through one or more adhesives, fasteners, bonding, and/or the like. In at least one other embodiment, the fluid inlet housing 104 and the fluid outlet housing 106 may be integrally molded and formed as a single piece, such as a unitary piece of injection-molded plastic.

The fluid inlet housing 104 includes a first fluid inlet port 108 and a second inlet port 110. The first fluid inlet port 108 includes an outer tubular wall 111 that defines a fluid inlet 112 that forms part of and leads into a fluid inlet channel 114. Similarly, the second fluid inlet port 110 includes an outer tubular wall 115 that defines a fluid inlet 116 that forms part of and leads into a fluid inlet channel 118.

The first and second fluid inlet ports 108 and 110 connect to a coupling base 120 that is coupled to a reciprocal coupling base 122 of the fluid outlet housing 106. The coupling base 122 connects to a fluid outlet port 124. The fluid outlet port 124 includes an outer tubular wall 125 that defines a fluid outlet 126 that forms part of and leads into a fluid outlet channel 128.

The fluid outlet port 124 includes a central longitudinal axis 130 that may be axially aligned with a central longitudinal axis of the check valve assembly 100. Central longitudinal axes 132 and 134 of the first fluid inlet port 108 and the second fluid inlet port 110, respectively, are offset from the central longitudinal axis 130 of the fluid outlet port 124. For example, the central longitudinal axis 132 is to one side of the central longitudinal axis 130, while the central longitudinal axis 134 is to an opposite side of the central longitudinal axis 130.

Figure 2:
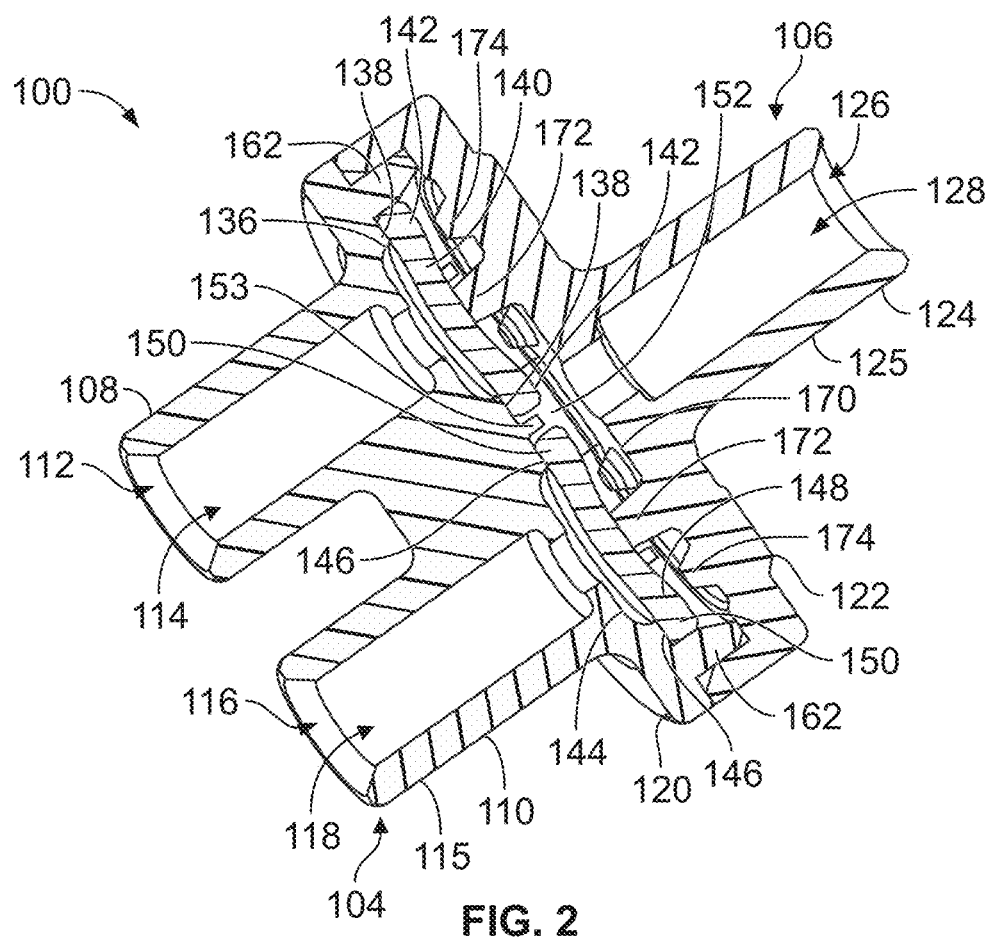
FIG. 2 illustrates a transverse cross-sectional view of a check valve assembly, according to an embodiment of the present disclosure.

FIG. 2 illustrates a transverse cross-sectional view of the check valve assembly 100. The fluid inlet channel 114 connects to a fluid opening 136 defined by an interior annular valve seat 138 of the coupling base 120. A first check valve in the form of a diaphragm 140 (which may be formed of rubber and disc shaped) extends over the fluid opening 136 in the closed position, such that an outer annular edge 142 seats on the valve seat 138. Similarly, the fluid inlet channel 118 connects to a fluid opening 144 defined by an interior annular valve seat 146 of the coupling base 120. A second check valve in the form of a diaphragm 148 (which may be formed of rubber and disc shaped) extends over the fluid opening 144 in the closed position, such that an outer annular edge 150 seats on the valve seat 146.

The fluid openings 136 and 144 connect to a central fluid chamber 152, which, in turn, connects to the fluid outlet channel 128. In operation, fluid passing through the fluid inlet channel 114 at sufficient fluid pressure causes the annular edge 142 to unseat from the valve seat 138. The fluid then passes from the fluid opening 136 into the central fluid chamber 152, and into the fluid outlet channel 128. Similarly, fluid passing through the fluid inlet channel 118 at sufficient fluid pressure causes the annular edge 150 to unseat from the valve seat 146. The fluid then passes from the fluid opening 144 into the central fluid chamber 152, and into the fluid outlet channel 128.

The diaphragms 140 and 148 prevent, minimize, or otherwise reduce the possibility of fluid within the fluid outlet channel 128 from passing back into the respective fluid openings 136 and 144. That is, to the extent that any fluid within the fluid outlet channel 128 tends to retreat back or back-flow towards the fluid openings 136 and/or 144, the back-flow pressure exerted into the diaphragms 140 and 148 increases the seating force of the diaphragms 140 and 148 into the respective valve seats 138 and 146, thereby preventing the fluid from passing into the fluid openings 136 and 144.

Figure 3:
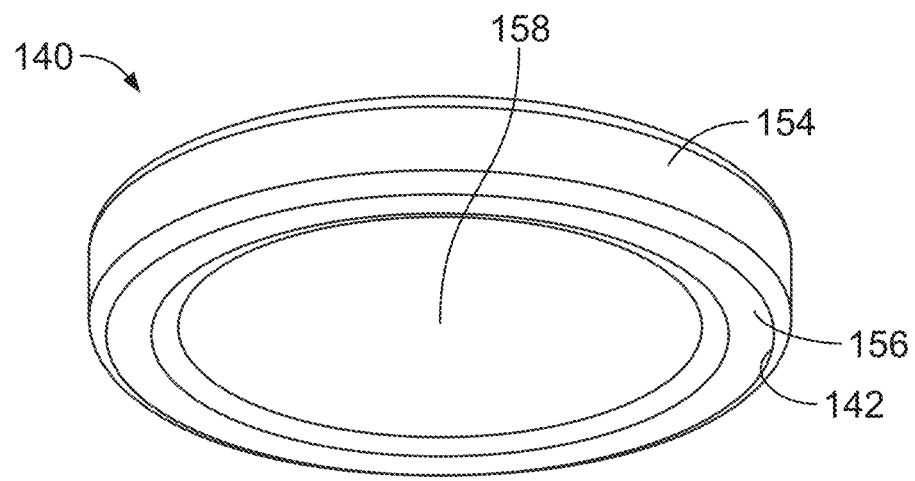
FIG. 3 illustrates a perspective bottom view of a diaphragm, according to an embodiment of the present disclosure.

FIG. 3 illustrates a perspective bottom view of the diaphragm 140, according to an embodiment of the present disclosure. While not shown in FIG. 3, the diaphragm 148 (shown in FIG. 2) may be constructed in the same manner as the diaphragm 140.

The diaphragm 140 includes an annular body 154 in which the outer annular edge 142 may include a raised or downwardly extending rim 156 that extends radially and below from a recessed central hub 158. Thus, the outer rim 156 is thicker than the central hub 158. While not shown in FIG. 3, the diaphragm 148 also includes an annular body in which an annular edge may include a raised or downwardly extending rim that extends below a recessed central hub. Referring to FIGS. 2 and 3, the raised rim 156 increases the contact area between the diaphragms 140, 148 and the respective valve seats 138 and 146, thereby providing increased, robust sealing therebetween.

Figure 4:
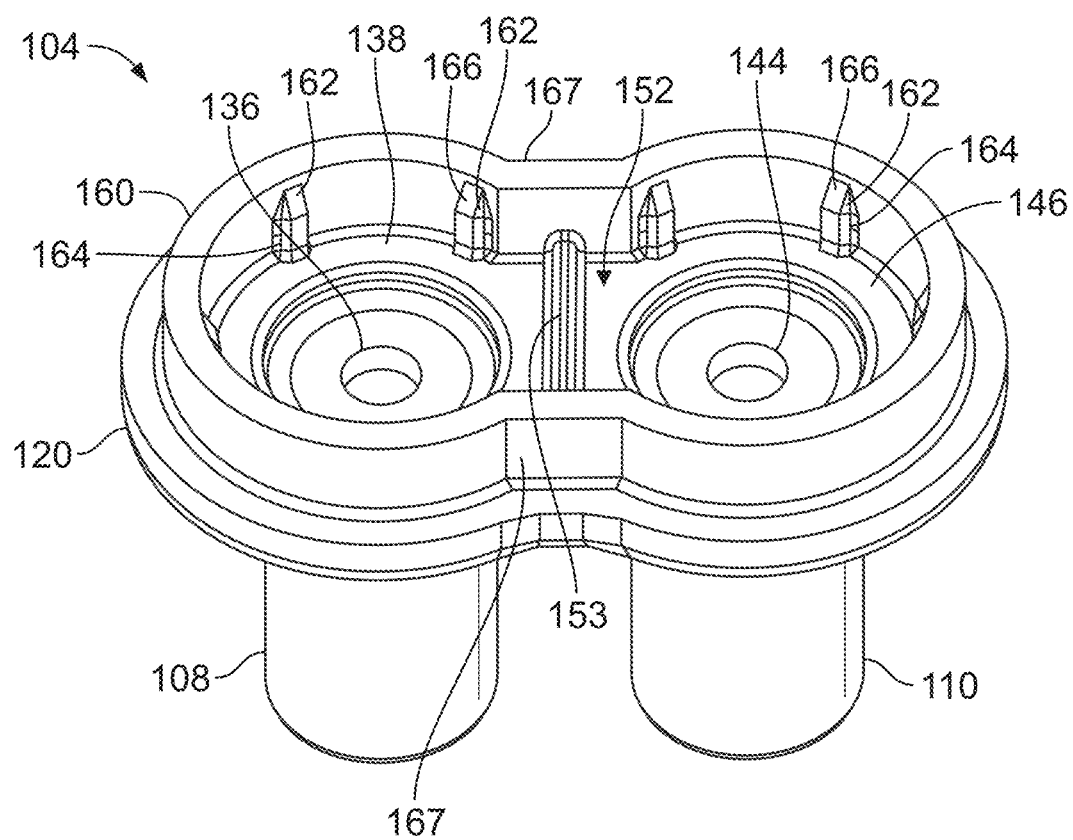
FIG. 4 illustrates a perspective top view of a fluid inlet housing, according to an embodiment of the present disclosure.

FIG. 4 illustrates a perspective top view of the fluid inlet housing 104, according to an embodiment of the present disclosure. The coupling base 120 includes an upstanding wall 160 surrounding the central fluid chamber 152. A plurality of guide ribs 162 inwardly extend from the wall 160 into the central fluid chamber 152. The guide ribs 162 may be regularly spaced about the wall 160. More or less guide ribs 162 than shown may be used.

Each of the diaphragms 140 and 148 (shown in FIG. 2) may be radially constrained (at least in part) between the guide ribs 162. Thus, the guide ribs 162 ensure that the diaphragms 140 and 148 are coaxially aligned over the respective fluid openings 136 and 144 and are configured to fully seat on the respective valve seats 138 and 146 in the closed positions.

Each of the guide ribs 162 includes a stem 164 extending upwardly from a valve seat 138 or 146. The stem 164 connects to a distal beveled tip 166. Referring to FIGS. 1 and 4, it has been found that the shape of the guide ribs 162 (including the stems 164 and the upper beveled tips 166) directs fluid flow up around the diaphragms 140 and 148 as the diaphragms 140 and 148 unseat from the valve seats 138 and 146.

As shown, a central deflecting barrier 153 (such as a rib, beam, wall, or other such barrier) may be disposed within the fluid chamber 152 between the fluid openings 136 and 144. The deflecting barrier 153 may span across the fluid chamber 152 between opposed wall segments 167. The deflecting barrier 153 deflects and redirects fluid flowing through the fluid opening 136 upwardly and away from the fluid opening 144, and vice versa. In this manner, the deflecting barrier 153 is configured to prevent undesired fluid mixing. The deflecting barrier 153 provides a barrier between the fluid openings 136 and 144 that reduces the possibility of fluid passing between the fluid openings 136 and 144.

Figure 5:
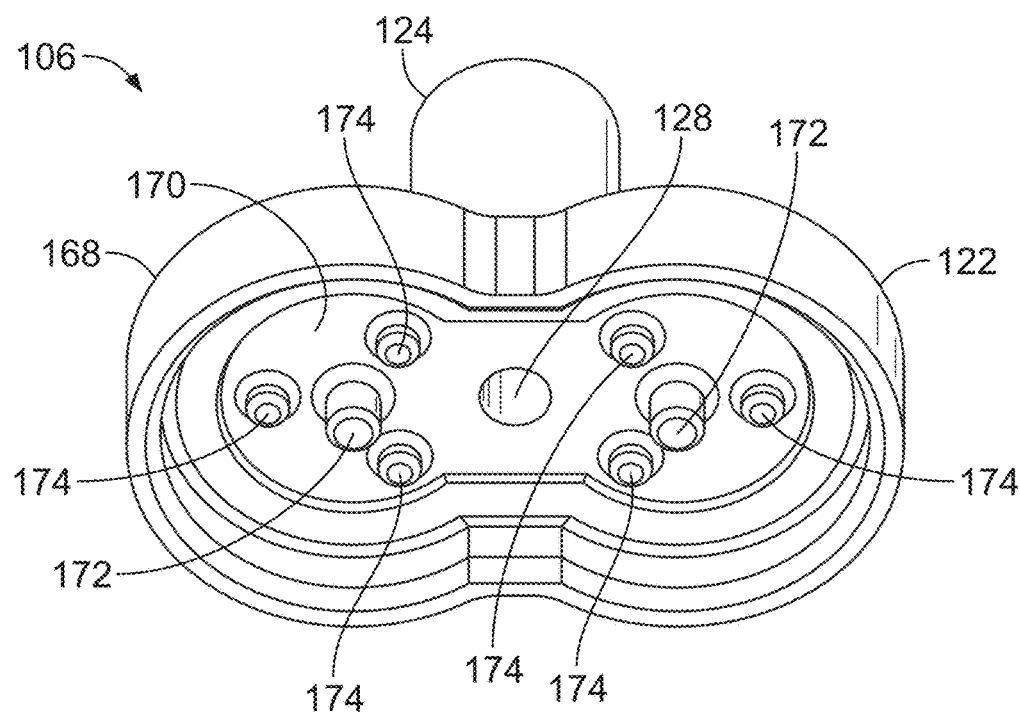
FIG. 5 illustrates a perspective bottom view of a fluid outlet housing, according to an embodiment of the present disclosure.

FIG. 5 illustrates a perspective bottom view of the fluid outlet housing 106, according to an embodiment of the present disclosure. The coupling base 122 includes an outer wall 168 surrounding a panel 170. Referring to FIGS. 2 and 5, a restraining protuberance 172 (for example, a central upstand such as such as a post, column, stud, nub, or the like) extends downwardly from the panel 170 above each of the diaphragms 140 and 148. The restraining protuberances 172 may be coaxially aligned with respective fluid inlet ports 108 and 110. The restraining protuberances 172 abut into centers of the diaphragms 140 and 148. In this manner, the restraining protuberances 172 maintain the diaphragms 140 and 148 over the fluid openings 136 and 144, whether the diaphragms 140 and 148 are in the closed or open positions.

A plurality of support protuberances 174 may extend downwardly from the panel 170. A plurality of support protuberances 174 (for example, upstands such as posts, columns, studs, nubs, or the like) may be positioned around each restraining protuberance 172. The support protuberances 174 may be regularly spaced around each restraining protuberance 172. More or less support protuberances 174 than shown may be used. In at least one embodiment, the fluid outlet housing 106 does not include any restraining protuberances 172.

The restraining protuberances 172 extend downwardly from the panel 170 a greater distance than do the support protuberances 174. When the diaphragms 140 and 148 are fully seated on the valve seats 138 and 146, respectively, the support protuberances 174 do not abut into the diaphragms 140 and 148 (whereas the restraining protuberances 172 abut into the diaphragms 140 and 148). As the diaphragms 140 and 148 are forced by fluid pressure off the valve seats 138 and 146, the outer annular portions of the diaphragms 140 and 148 may upwardly deflect into the support protuberances 174. In this manner, the support protuberances 174 may be sized and shaped to control deflection of the diaphragms 140 and 148, such as to control a flow rate of fluid out of the fluid openings 136 and 144 and/or maintain the resilience of the diaphragms 140 and 148. The support protuberances 174 are configured to prevent, minimize, or otherwise reduce the possibility that the diaphragms 140 and 148 flex beyond their elastic limits when subjected to increased outwardly-flowing fluid pressures and flows.

Figure 6:
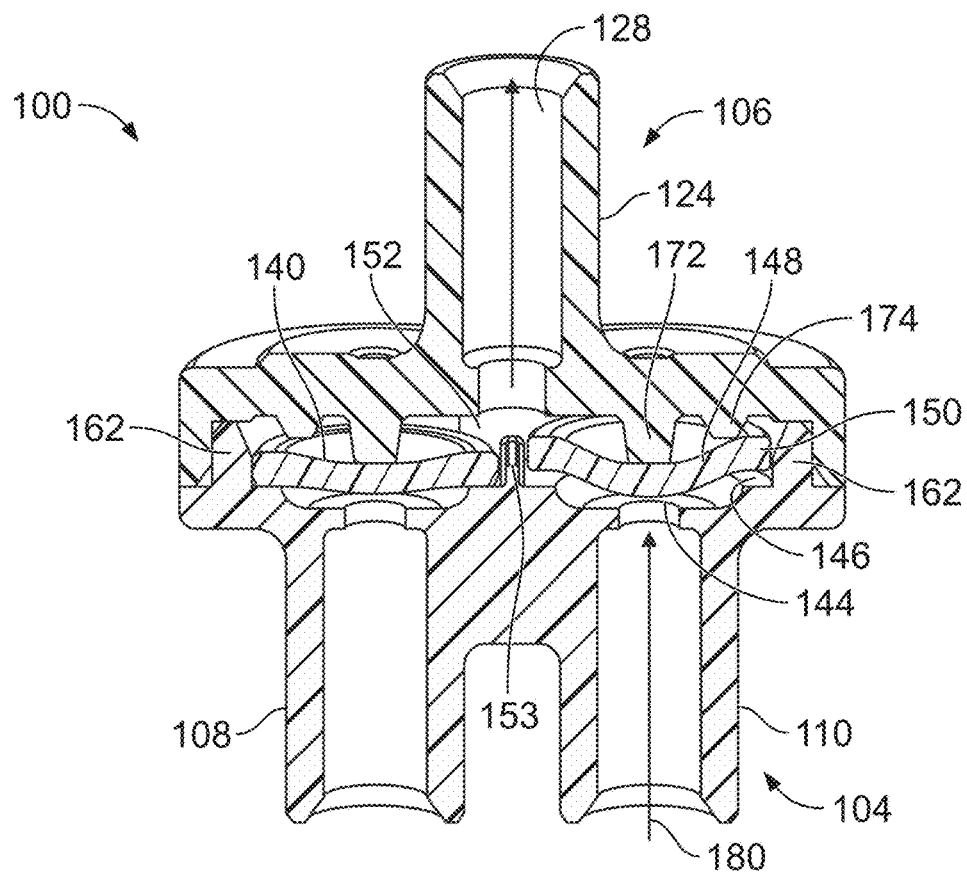
FIG. 6 illustrates a perspective cross-sectional view of a check valve assembly, according to an embodiment of the present disclosure.
Figure 7:
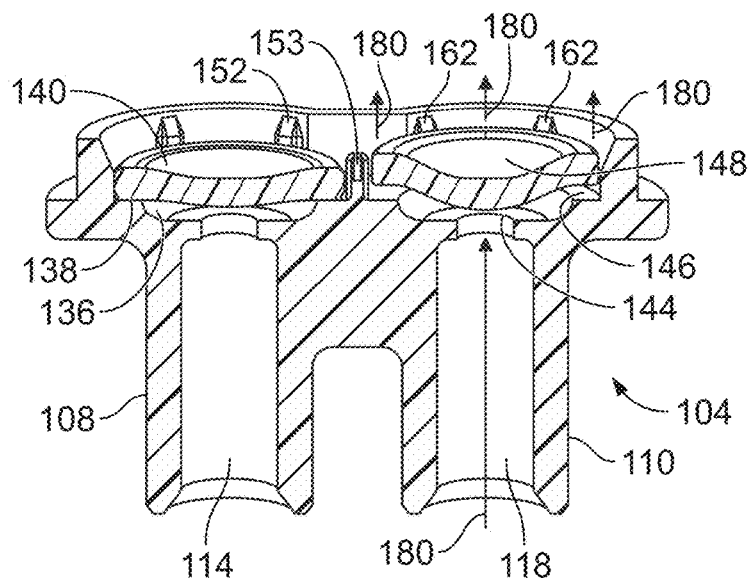
FIG. 7 illustrates a perspective cross-sectional view of a fluid inlet housing, according to an embodiment of the present disclosure.

FIG. 6 illustrates a perspective cross-sectional view of the check valve assembly 100. FIG. 7 illustrates a perspective cross-sectional view of the fluid inlet housing 104. Referring to FIGS. 6 and 7, fluid 180 is shown flowing into the fluid inlet channel 118 of the fluid inlet port 110. The fluid is of sufficient fluid pressure to unseat the annular edge 150 of the diaphragm 148 off the valve seat 146, thereby allowing the fluid 180 to flow around the annular edge 150 into the central fluid chamber 152 and into the fluid outlet channel 128. As shown, the restraining protuberance 172 abuts into a central portion (such as the central hub 158) of the diaphragm 148, thereby ensuring that the diaphragm remains centered over the fluid opening 144. The annular edge 150 may be forced into the support protuberances 174, which control the upward deflection of the diaphragm 148, as noted above.

Because fluid is not flowing through the fluid inlet channel 114, the diaphragm 140 remains seated on the valve seat 138. As such, the fluid 180 is unable to back-flow into the fluid inlet channel 114. The guide ribs 162 guide the flow of the fluid 180 into the fluid outlet channel 128.

When fluid flows through the fluid inlet channel 114 of sufficient force, operation of the diaphragms 140 and 148 is opposite than described above. That is, when fluid flows through fluid inlet channel 114, the diaphragm 140 unseats (thereby allowing fluid to flow around the diaphragm 140 and into the fluid outlet channel 128), while the diaphragm 148 remains seated (thereby preventing fluid from back-flowing into the fluid inlet channel 118).

When fluid pressure in either of the fluid inlet channels 114 or 118 rises above an opening threshold, the diaphragms 140 and 148 deflect away from the valve seats 138 and 146 open a fluid path to the fluid outlet channel 128. In at least one embodiment, the opening pressure specification range used in a CT set may be 1.5-6 pounds per square inch (psi). Optionally, the opening pressure may be adjusted by varying the thickness and/or shore hardness of the diaphragms 140 and 148, and/or the height of the restraining protuberance 172, which imparts pretension onto the diaphragms 140 and 148.

Fluid flow is uniformly directed to and around the outer periphery of the diaphragms 140 and 148 to minimize or otherwise reduce areas of restricted flow. The deflecting barrier 153 prevents flow from the active/open side of the check valve assembly 100 peeling open the diaphragm on the inactive/closed side. The deflecting barrier 153 is configured to deflect fluid flow, but does not cause a significant area of non-flow or dead space.

Figure 8:
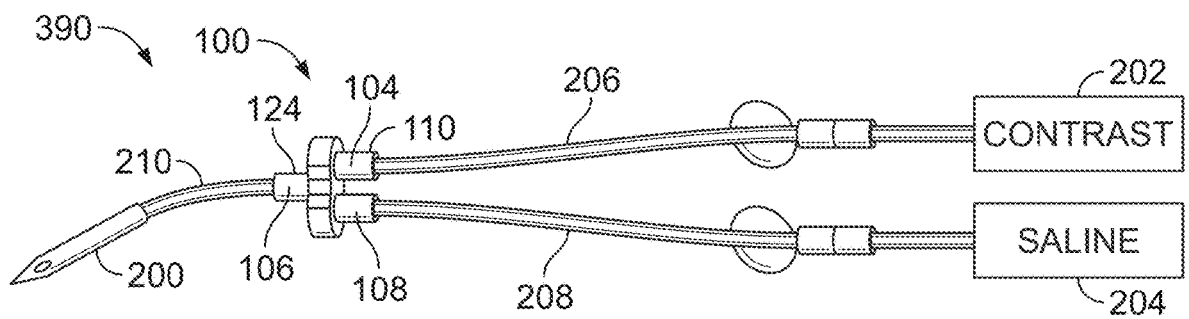
FIG. 8 illustrates a lateral view of a fluid delivery system, according to an embodiment of the present disclosure.

FIG. 8 illustrates a lateral view of a fluid delivery system 390, according to an embodiment of the present disclosure. The fluid delivery system 390 includes the check valve assembly 100 connecting a syringe 200 to a contrast agent container 202 and a saline container 204. The syringe 200 is configured to be inserted into anatomy (such as a vein) of an individual. The contrast agent container 202 contains liquid contrast agent. The saline container 204 includes liquid saline. Optionally, the containers 202 and 204 may contain different fluids.

Referring to FIGS. 1-8, the fluid inlet channel 118 of the fluid inlet port 110 is fluidly connected to the contrast container 202. The fluid inlet channel 114 of the fluid inlet port 108 is fluidly connected to the saline container 204. The fluid outlet channel 128 of the fluid outlet port 124 is fluidly connected to the syringe 200.

The contrast agent container 202 connects to the fluid inlet port 110 through a tube 206, while the saline container 204 connects to the fluid inlet port 108 through a tube 208. The syringe connects to the fluid outlet port 124 through a tube 210.

When contrast agent is delivered from the contrast agent container 202 at sufficient fluid pressure, the check valve assembly 100 allows the contrast agent to flow towards and into the syringe 200, while preventing the contrast agent from back-flowing into the fluid inlet port 108, as described above. Similarly, when saline is delivered from the saline container 204 at sufficient fluid pressure, the check valve assembly 100 allows the saline to flow towards and into the syringe 200, while preventing the saline from back-flowing into the fluid inlet port 110.

The check valve assembly 100 may be coupled to a Computed Tomography (CT) set (such as through solvent bonding). As such, the check valve assembly 100 provides a back check and an anti-siphon function. The check valve assembly 100 may replace two single check valves and a separate and distinct "Y" connector joint. The dual check assembly 100 integrates the two diaphragms 140 and 148 with respect to the respective fluid inlet channels 114 and 118, instead of positioning separate and distinct check valves in saline and contrast lines.

Figure 9:
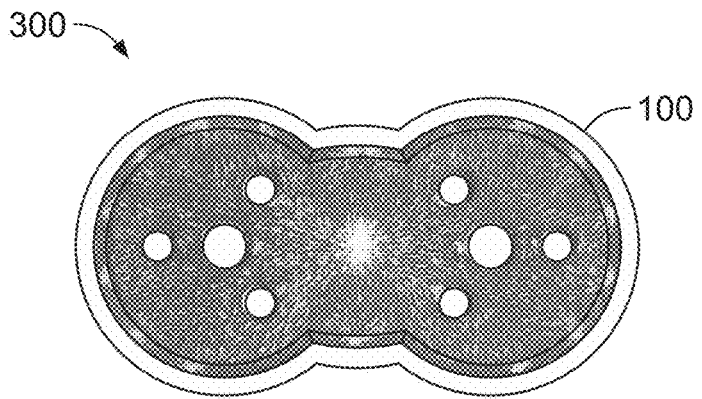
FIG. 9 illustrates a flow vector plot for a check valve assembly, according to an embodiment of the present disclosure.

FIG. 9 illustrates a flow vector plot 300 for the check valve assembly 100, according to an embodiment of the present disclosure. A Fluid Structure Interaction (FSI) simulation was conducted in which a number of different fluid exit geometries were considered. Based on the FSI, the geometry of the fluid outlet housing 106 (shown in FIG. 1, for example) provides efficient fluid flow, and ensures that areas of non-flow (or dead space) are minimized or otherwise reduced.

Figure 10:
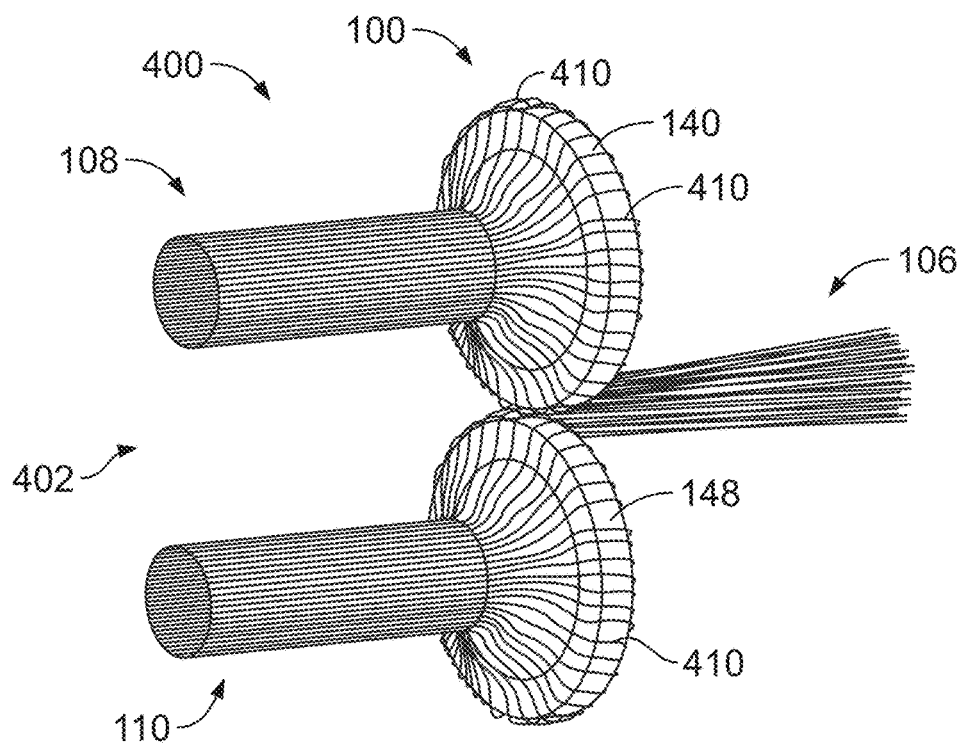
FIG. 10 illustrates a streamline plot from a fluid inlet side for flow through a check valve assembly with both fluid inlet ports open, according to an embodiment of the present disclosure.
Figure 11:
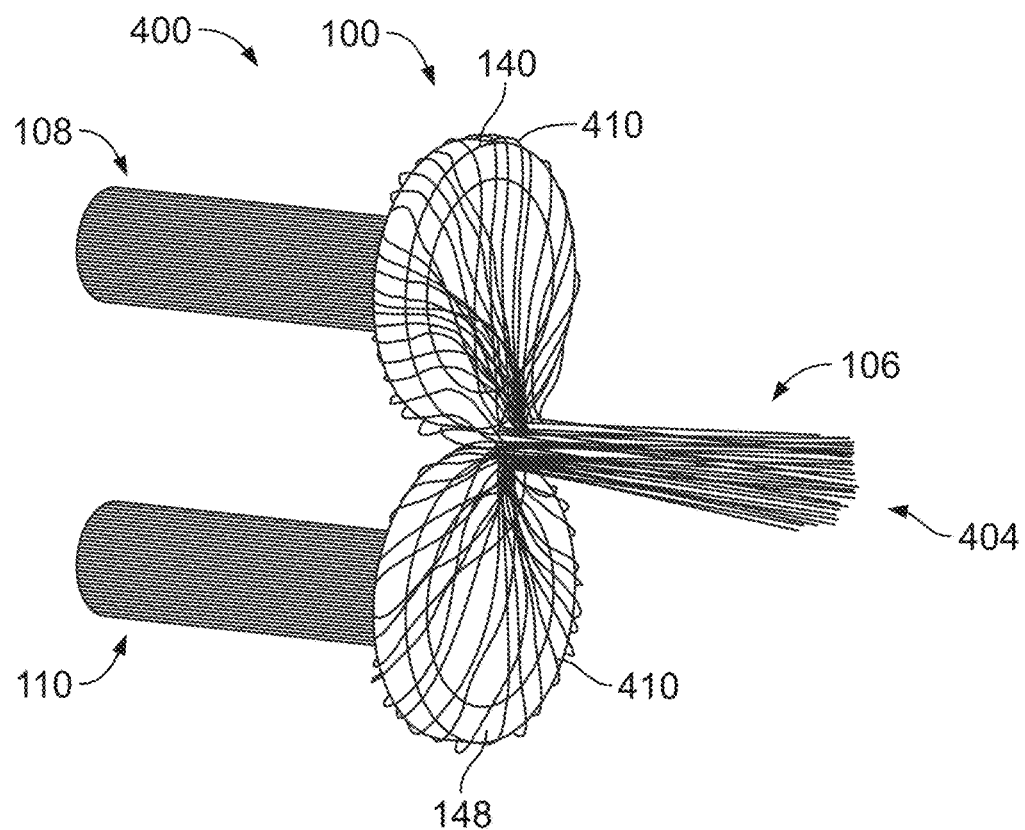
FIG. 11 illustrates a streamline plot from a fluid outlet side for flow through a check valve assembly with both fluid inlet ports open, according to an embodiment of the present disclosure.

FIG. 10 illustrates a streamline plot 400 from a fluid inlet side 402 for flow 410 through the check valve assembly 100 with both fluid inlet ports open 108 and 110, according to an embodiment of the present disclosure. FIG. 11 illustrates the streamline plot 400 from a fluid outlet side 404 for flow 410 through the check valve assembly 100 with both fluid inlet ports 108 and 110 open. As shown in FIGS. 10 and 11, fluid flow 410 is directed to the outer perimeters of the diaphragms 140 and 148, thereby eliminating, minimizing, or otherwise reducing areas of non-flow or dead space.

Embodiments of the present disclosure provide a check valve assembly that combines the function of two standard check valves and one Y site component into a single assembly. Typically, known check valves have three components—a fluid entry, a rubber sealing member (disc, diaphragm or umbrella) and a fluid exit. As such, two standard check valves and a Y connector result in seven separate and distinct components. In contrast, certain embodiments of the present disclosure provide a check valve assembly having four components, thereby reducing the total number of individual components (that is, two check valves and one Y connector) to four.

Certain embodiments of the present disclosure provide a dual check valve assembly including one or more deflecting barriers that are configured to prevent flow from the active/open side of the valve peeling open the second diaphragm on the inactive/closed side. The deflecting barrier deflects the fluid flow, but does not cause a significant area of non-flow or dead space.

The check valve assembly may also include guide ribs that are configured to direct fluid flow up around unseated diaphragms. Further, the diaphragms may include raised annular surfaces that increase the contact area between the diaphragms and the valve seats.

On the fluid exit, restraining protuberances, such as circular central upstands, may be used to impart pretension onto the diaphragms but do not excessively disturb the flow through the check valve assembly. Also, the check valve assembly may include support protuberances, such as circular support upstands, that prevent the diaphragms from flexing beyond their elastic limits, but do not excessively disturb fluid flow through the check valve assembly.

Embodiments of the present disclosure provide a check valve assembly that reduces possibility of: micro bubble accumulation, contrast/saline mixing, and back pressure in the line. In contrast, known CT sets include a Y site or similar junction geometry that is susceptible to having areas of restricted flow. Micro bubbles can accumulate in the areas of restricted flow and form a potentially hazardous larger bubble. Embodiments of the present disclosure provide a check valve assembly that replaces such junctions and eliminates, minimizes, or otherwise reduces areas of restricted flow. As such, the chances of micro bubbles accumulating are eliminated, minimized, or otherwise reduced.

Also, the junctions in existing CT sets are also susceptible to allowing droplets of liquid from the inactive line being drawn into the flow from the active line. The mixing of contrast media from one line with saline from the second line can pose problems in trying to complete a CT scan. Embodiments of the present disclosure provide a check valve assembly at the junction, which reduces the possibility of droplets of liquid being drawn from the inactive line.

Integrating the check valve assembly into a CT set lowers back pressure for a given flow rate when compared with traditional CT sets which have two standard check valves and a Y site. As such, there is a lower chance of a pump generating an alarm due to over-pressurization while trying to reach an adequate flow rate for the procedure.

Embodiments of the present disclosure provide a significant cost savings over known systems, as the check valve assembly replaces two externally sourced check valves and a Y connection joint. The check valve assembly also reduces the number of assembly steps involved in the manufacture of the CT sets.

It has been found that the check valve assembly according to embodiments of the present disclosure substantially reduces available fluid for mixing in comparison to prior systems. By joining two fluid lines with the check valve assembly, the likelihood of the two fluids mixing is substantially reduced. Embodiments of the present disclosure provide a check valve assembly that eliminates, minimizes, or otherwise reduces residual fluid volume therein.

As described above, embodiments of the present disclosure provide a check valve assembly that prevents, minimizes, or otherwise reduces the possibility of saline and contrast undesirably mixing. Embodiments of the present disclosure provide a check valve assembly that prevents, minimizes, or otherwise reduces the possibility of image false positives, such as may be caused by spots formed by contrast agent. Overall, embodiments of the present disclosure provide a simpler and more effective check valve assembly in comparison to known systems and methods.

Figure 12:
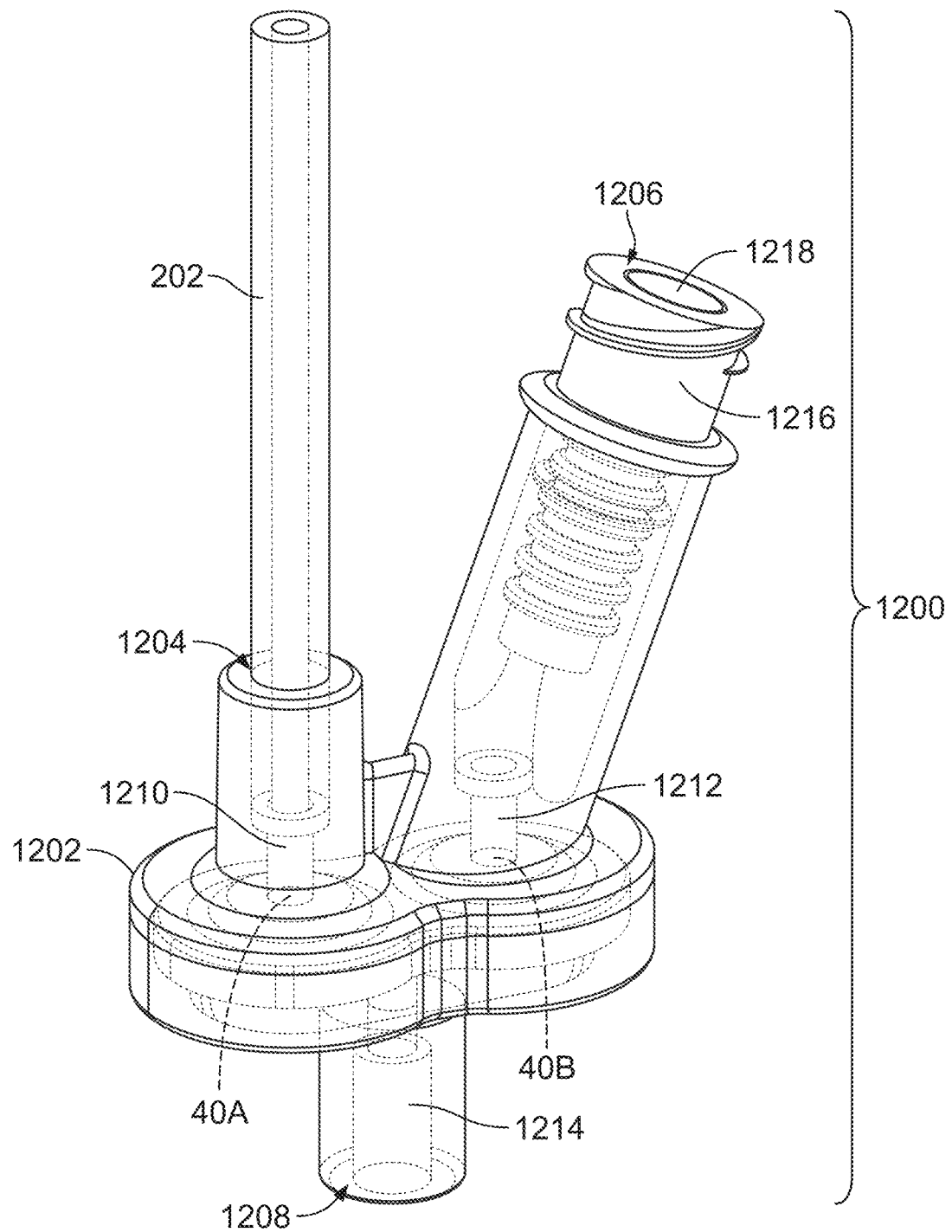
FIG. 12 illustrates one embodiment of a check valve assembly.

FIG. 12 illustrates one embodiment of a check valve assembly 1200. The check valve assembly 1200 can be an infusion set check valve assembly that is used with or is included in an infusion set that uses a pump or gravity to intravenously or subcutaneously deliver one or more fluids to a patient. The check valve assembly 1200 has a body formed as a housing 1202. The housing 1202 has a Y-shape in the illustrated embodiment, but alternatively may have another shape.

The housing 1202 is shaped to define two or more inlet ports and at least one outlet port. In the illustrated embodiment, the housing 1202 defines two inlet ports 1204, 1206 and one outlet port 1208. The inlet ports 1204 provide openings or access into the housing 1202 and the outlet port 1208 defines a single opening leading out of the housing 1202. Each of the inlet ports 1204, 1206 can be fluidly coupled with a different container (e.g., the containers 202, 204) by one or more conduits, such as the tubes 206, 208. Each of the inlet ports 1204, 1206 can receive a fluid (e.g., a liquid) from a different container (e.g., a different intravenous or IV bag, syringe, etc., such as the container 202 or 204) which is combined within the housing 1202 and the fluid or fluids are output from the housing 1202 (e.g., to a patient) via the outlet port 1208.

For example, each inlet port 1204, 1206 defines a separate inlet channel 1210, 1212 inside the housing 1202 and which the different fluids can be received from different containers 202, 204 that retain the fluids. The fluids can combine within the housing 1202 and exit out of the housing 1202 via an outlet channel 1214 that is defined by the outlet port 1208. Or, if fluid is only received through one of the inlet port 1204 or 1206 and one of the inlet channels 1210 or 1212, then only one of the fluids may exit the housing 1202 via the outlet port 1208. The outlet port 1208 can be fluidly coupled with a conduit that is connected with a patient, such as a patient line (e.g., the tube 210), to deliver the fluid or combined fluids to the patient.

At least one check valve (e.g., the diaphragm 40) may be disposed within the housing 1202 between the outlet channel 1214 and at least one of the first inlet channel 1210 or the second inlet channel 1212. In the illustrated embodiment, there is a first check valve (e.g., a first diaphragm 40A) between the first inlet channel 1210 and the outlet channel 1214 and a second check valve (e.g., a second diaphragm 40B) between the second inlet channel 1212 and the outlet channel 1214. Each check valve opens for the fluid flowing in the corresponding inlet channel 1210 or 1212 to pass through the check valve and into the outlet channel 1214. For example, responsive to a fluid being forced through the first inlet channel 1210 by a pump, by manual application of pressure on a syringe or on a bag (e.g., an IV bag), by gravity, etc., a first check valve between the first inlet channel 1210 and the outlet channel 1214 opens to permit the fluid to flow out of the housing 1202 through the outlet channel 1214 and the outlet port 1208. Responsive to this fluid no longer being forced or flowing into the first inlet channel 1210 at a pressure that exceeds a pressure threshold of the first check valve, the first check valve may close to prevent the fluid from flowing into the outlet channel 1214. Similarly, responsive to a fluid being forced through the second inlet channel 1212 by a pump, by manual application of pressure on a syringe or on a bag, by gravity, etc., a second check valve between the second inlet channel 1212 and the outlet channel 1214 opens to permit the fluid to flow out of the housing 1202 through the outlet channel 1214 and the outlet port 1208. Responsive to this fluid no longer being forced or flowing into the second inlet channel 1212 at a pressure that exceeds a pressure threshold of the second check valve, the second check valve may close to prevent the fluid from flowing into the outlet channel 1214.

The check valves may not open when pressure from a fluid is applied in the reverse direction. Backflow from the patient line coupled with the outlet channel 1214 up into the housing 1202 may be blocked from entering either the first or second inlet channels 1210, 1212 by the corresponding first or second check valve. For example, backflow entering the outlet channel 1214 can be blocked by the first check valve from entering the first inlet channel 1210 and backflow entering the outlet channel 1214 can be blocked by the second check valve from entering the second inlet channel 1212.

The check valves may open responsive to the same cracking pressures. Alternatively, each of the check valves may open responsive to a different cracking pressure (e.g., one check valve may open at a lower cracking pressure than the other check valve). The check valves may have large or small cracking pressures. For example, the check valves may open to relatively low cracking pressures such as twenty to fifty centimeters of head pressure. As another example, the check valves may open to pressures imparted by a gravity feed set.

The check valves can be positioned to prevent the fluid in one inlet channel 1210 or 1212 from backflowing into the other inlet channel 1212 or 1210. For example, the first check valve can be sealed to the end of the first inlet channel 1210 such that no fluid in the second inlet channel 1212 can pass through the first check valve and up into the first inlet channel 1210. Similarly, the second check valve can be sealed to the end of the second inlet channel 1212 such that no fluid in the first inlet channel 1210 can pass through the second check valve and up into the second inlet channel 1212.

In the illustrated embodiment, the second inlet port 1206 includes a connector 1216 configured to mate with a complementary connector. This connector 1216 can be formed as part of the housing 1202 or can be a separate component coupled (e.g., fused, adhered, or otherwise coupled) with the housing 1202. The connector 1216 shown in FIG. 12 is a threaded connection shaped to mate with another connector having a complementary thread or threaded connection. Optionally, the second inlet port 1206 can have an elastomer membrane 1218 that seals the second inlet channel 1212 from the ambient environment. This membrane 1218 can be punctured (e.g., by a syringe needle) to allow fluid to pass the membrane 1218 into the second inlet channel 1212.

The housing 1202 can be a self-contained housing. For example, all components of the check valve assembly 1200 may be contained within the housing 1202 and no components or parts of the check valve assembly 1200 may be outside of the housing 1202. Alternatively, the housing 1202 may not be self-contained in another embodiment, where the housing 1202 is formed from multiple parts coupled together and separable from each other without destroying the check valve assembly 1200.

The housing 1202 may be relatively small in that the ports 1204, 1206, 1208 and channels 1210, 1212, 1214 are close to each other. For example, the first inlet port 1204, the second inlet port 1206, and the outlet port 1208 may be closer to each other within the housing 1202 than a first linear distance between from the first inlet port 1204 to a first container that is fluidly coupled with the first inlet port 1204 by a tube or line (that connects the first inlet port 1204 with the container), closer to each other than a second linear distance from the second inlet port 1206 to a second container along a tube or line (that connects the second inlet port 1206 to the second container), and/or closer to each other than a third linear distance from the outlet port 1208 to a patient along the patient line that connects the outlet port 1208 to the patient. The largest linear distance between any two of the ports 1204, 1206, 1208 can be shorter than the shortest of these first, second, or third distances.

Figure 13:
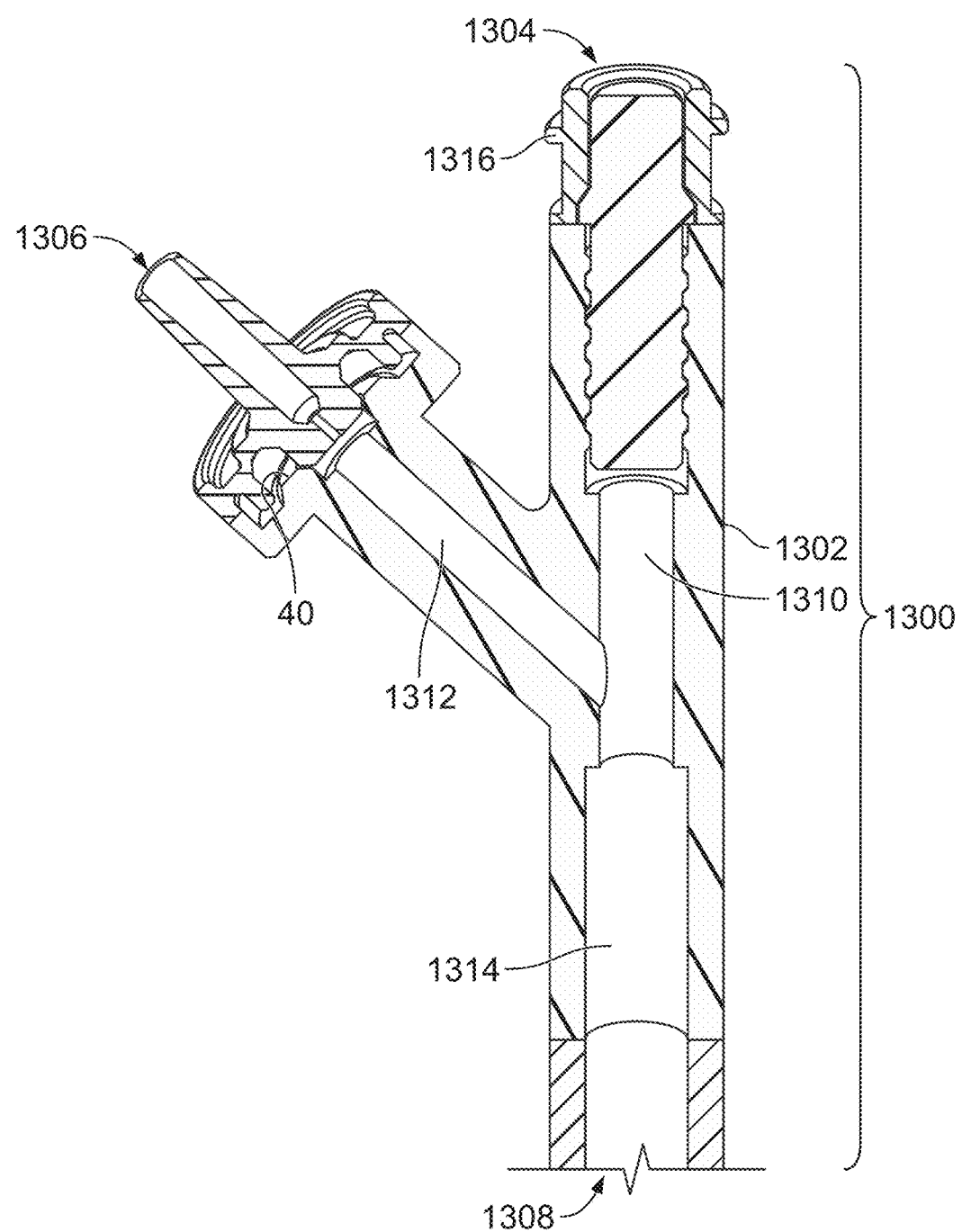
FIG. 13 illustrates one embodiment of a check valve assembly.

FIG. 13 illustrates one embodiment of a check valve assembly 1300. Similar to the check valve assembly 1200, the check valve assembly 1300 can be an infusion set check valve assembly that is used with or is included in an infusion set that uses a pump or gravity to intravenously or subcutaneously deliver one or more fluids to a patient. The check valve assembly 1300 also has a Y-shaped body formed as a housing 1302.

The housing 1302 also define two or more inlet ports and at least one outlet port. In the illustrated embodiment, the housing 1302 defines two inlet ports 1304, 1306 and one outlet port 1308. Each of the inlet ports 1304, 1306 can be fluidly coupled with a different container by one or more conduits to receive fluids into separate inlet channels 1310, 1312, as described above. One or more of the inlet ports 1306, 1308 may include a connector and/or membrane, as described above. The housing 1302 can be a self-contained and/or small housing, as described above in connection with the housing 1202.

In contrast to the check valve assembly 1200, the check valve assembly 1300 includes fewer check valves than inlet channels 1310, 1312 and fewer check valves than inlet ports 1304, 1306. For example, the check valve assembly 1300 shown in FIG. 13 includes a single check valve (e.g., diaphragm 40). This check valve can open responsive to fluid entering the second inlet port 1306 and the second inlet channel 1312 at a pressure that is at least as great as a cracking pressure of the check valve. The check valve can close or remain closed responsive to the pressure of this fluid decreasing below the cracking pressure of the check valve.

The check valve can prevent backflow from an outlet channel 1314 from flowing into the second inlet channel 1312. For example, patient backflow in the tube connecting the patient to the outlet channel 1314 of the housing 1302 via the outlet port 1308 is prevented from entering the second inlet channel 1312 (and thereby prevented from exiting the housing 1302 via the second inlet port 1306) by the check valve. The check valve can be positioned within the second inlet channel 1312 so that the check valve prevents the fluid in the first inlet channel 1310 from flowing out of the housing 1302 via the second inlet port 1306. For example, without the check valve, a blockage in the patient line may cause the fluid flowing in the first inlet channel 1310 to backflow into the second inlet channel 1312, out of the housing 1302 via the second inlet port 1306, and into the tube connecting the second inlet port 1306 with a container. With the check valve, the blockage in the patient line does not cause the fluid flowing in the first inlet channel 1310 to backflow into the second inlet channel 1312, out of the housing 1302 via the second inlet port 1306, or into the tube connecting the second inlet port 1306 with the container.

In one embodiment, an infusion set check valve assembly includes a self-contained housing that defines at least a first inlet port, a second inlet port, and a fluid outlet port. The first inlet port defines a first inlet channel through which a first fluid is received from a first container that retains the first fluid. The second inlet port defines a second inlet channel through which a second fluid is received from a second container that retains the second fluid. The outlet port defines an outlet channel through which one or more of the first fluid or the second fluid received into the self-contained housing via one or more of the first inlet port or the second inlet port is directed to a patient line. The assembly also includes at least one check valve disposed within the self-contained housing between the outlet channel and at least one of the first inlet channel or the second inlet channel. The at least one check valve is configured to open for the first fluid to flow from the first inlet channel to the patient line via the outlet channel while the second fluid also flows from the second inlet channel to the patient line via the outlet channel. The at least one check valve is configured to close to prevent the first fluid from flowing from the first inlet channel to the patient line via the outlet channel while the second fluid flows from the second inlet channel to the patient line via the outlet channel.

Optionally, the at least one check valve includes only a single check valve in the self-contained housing, the single check valve located between the first inlet channel and the outlet channel such that the single check valve permits the second fluid to flow from the second inlet channel to the outlet channel regardless of whether the single check valve is open or closed.

Optionally, the at least one check valve includes a first check valve and a second check valve in the self-contained housing, the first check valve located between the first inlet channel and the outlet channel, the second check valve located between the second inlet channel and the outlet channel.

Optionally, the first check valve and the second check valve prevent the first fluid from backflowing into the second inlet channel and prevent the second fluid from backflowing into the first inlet channel responsive to a blockage occurring in the patient line.

Optionally, the second inlet port includes one or more of a connector configured to mate with a complementary connector fluidly coupled with the second container or a membrane configured to permit passage therethrough of a syringe needle to receive the second fluid.

Optionally, the first inlet port, the second inlet port, and the outlet port are closer to each other within the self-contained housing than the first inlet port is to the first container along a first line that connects the first inlet port to the first container, closer to each other than the second inlet port is to the second container along a second line that connects the second inlet port to the second container, and closer to each other than the outlet port is to a patient along the patient line that connects the outlet port to the patient.

Optionally, the at least one check valve is configured to open responsive to receiving the first fluid from a gravity feed set that includes the first container.

Optionally, the self-contained housing has a Y-shape.

Optionally, the outlet channel is configured to be connected to the patient line for infusion of fluids in the first container and the second container to a patient via the patient line, wherein the at least one check valve prevents backflow from the patient line into at least one of the first container or the second container from the patient line.

Optionally, the self-contained housing is configured to be disposed at a distal end or a proximal end of an intravenous (IV) set.

In one embodiment, an infusion set fluid delivery system includes a first container configured to retain a first fluid and an infusion set check valve assembly that includes a self-contained housing defining at least a first inlet port, a second inlet port, and a fluid outlet port. The first inlet port defines a first inlet channel through which the first fluid is received from the first container. The second inlet port defines a second inlet channel through which a second fluid is received from a second container that retains the second fluid. The outlet port defines an outlet channel through which one or more of the first fluid or the second fluid received into the self-contained housing via one or more of the first inlet port or the second inlet port is directed to a patient line. The infusion set check valve assembly also includes at least one check valve disposed within the self-contained housing between the outlet channel and at least one of the first inlet channel or the second inlet channel. The at least one check valve is configured to open for the first fluid to flow from the first inlet channel to the patient line via the outlet channel while the second fluid also flows from the second inlet channel to the patient line via the outlet channel. The at least one check valve is configured to close to prevent the first fluid from flowing from the first inlet channel to the patient line via the outlet channel while the second fluid flows from the second inlet channel to the patient line via the outlet channel.

Optionally, the at least one check valve includes only a single check valve in the self-contained housing, the single check valve located between the first inlet channel and the outlet channel such that the single check valve permits the second fluid to flow from the second inlet channel to the outlet channel regardless of whether the single check valve is open or closed.

Optionally, the at least one check valve includes a first check valve and a second check valve in the self-contained housing, the first check valve located between the first inlet channel and the outlet channel, the second check valve located between the second inlet channel and the outlet channel.

Optionally, the first check valve and the second check valve prevent the first fluid from backflowing into the second inlet channel and prevent the second fluid from backflowing into the first inlet channel responsive to a blockage occurring in the patient line.

Optionally, the second inlet port includes one or more of a connector configured to mate with a complementary connector fluidly coupled with the second container or a membrane configured to permit passage therethrough of a syringe needle to receive the second fluid.

Optionally, the first inlet port, the second inlet port, and the outlet port are closer to each other within the self-contained housing than the first inlet port is to the first container along a first line that connects the first inlet port to the first container, closer to each other than the second inlet port is to the second container along a second line that connects the second inlet port to the second container, and closer to each other than the outlet port is to a patient along the patient line that connects the outlet port to the patient.

Optionally, the at least one check valve is configured to open responsive to receiving the first fluid from a gravity feed set that includes the first container.

Optionally, the self-contained housing has a Y-shape.

In one embodiment, an infusion set check valve assembly includes a self-contained housing that defines at least a first inlet port, a second inlet port, and a fluid outlet port. The first inlet port defines a first inlet channel through which a first fluid is received from a first container that retains the first fluid. The second inlet port defines a second inlet channel through which a second fluid is received from a second container that retains the second fluid. The outlet port defines an outlet channel through which one or more of the first fluid or the second fluid received into the self-contained housing via one or more of the first inlet port or the second inlet port is directed to a patient line. The assembly also includes a first check valve located between the first inlet channel and the outlet channel and a second check valve located between the second inlet channel and the outlet channel. The first check valve is configured to open for the first fluid to flow from the first inlet channel to the patient line via the outlet channel while the second check valve opens for the second fluid to concurrently flow from the second inlet channel to the patient line via the outlet channel. The first check valve is configured to close to prevent the first fluid from flowing from the first inlet channel to the patient line via the outlet channel while the second check valve remains open for the second fluid to continue flowing from the second inlet channel to the patient line via the outlet channel.

Optionally, the first check valve and the second check valve prevent the first fluid from backflowing into the second inlet channel and prevent the second fluid from backflowing into the first inlet channel responsive to a blockage occurring in the patient line.

Optionally, the second inlet port includes one or more of a connector configured to mate with a complementary connector fluidly coupled with the second container or a membrane configured to permit passage therethrough of a syringe needle to receive the second fluid.

Optionally, the first check valve is configured to open responsive to receiving the first fluid from a gravity feed set that includes the first container.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

Variations and modifications of the foregoing are within the scope of the present disclosure. It is understood that the embodiments disclosed and defined herein extend to all alternative combinations of two or more of the individual features mentioned or evident from the text and/or drawings. All of these different combinations constitute various alternative aspects of the present disclosure. The embodiments described herein explain the best modes known for practicing the disclosure and will enable others skilled in the art to utilize the disclosure. The claims are to be construed to include alternative embodiments to the extent permitted by the prior art.

To the extent used in the appended claims, the terms "including" and "in which" are used as the plain-English equivalents of the respective terms "comprising" and "wherein." Moreover, to the extent used in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

Various features of the disclosure are set forth in the following claims.

What is claimed is:

1. An infusion set check valve assembly comprising:
a self-contained housing that defines at least a first inlet port, a second inlet port, and a fluid outlet port, the first inlet port defining a first inlet channel through which a first fluid is received from a first container that retains the first fluid, the second inlet port defining a second inlet channel through which a second fluid is received from a second container that retains the second fluid, the outlet port defining an outlet channel through which one or more of the first fluid or the second fluid received into the self-contained housing via one or more of the first inlet port or the second inlet port is directed to a patient line;
a first check valve disposed within the self-contained housing between the outlet channel and the first inlet channel; and
a second check valve disposed within the self-contained housing between the outlet channel and the second inlet channel,
wherein the first check valve controls flow of the first fluid from the first inlet channel to the patient line via the outlet channel and the second check valve controls flow of the second fluid from the second inlet channel to the patient line via the outlet channel,
wherein the first check valve closes and prevents flow of the first fluid from the first inlet channel to the patient line via the outlet channel and the second check valve closes and prevents flow of the second fluid flows from the second inlet channel to the patient line via the outlet channel,
wherein each of the first check valve and the second check valve includes a diaphragm, a restraining protuberance, and one or more support protuberances, the restraining protuberance abutting a center of the diaphragm, the one or more support protuberances disposed radially outward of the restraining protuberance, the restraining protuberance being longer than the one or more support protuberances, wherein the one or more support protuberances are sized to limit deflection of an outer annular portion of the diaphragm in that the outer annular portion of the diaphragm contacts the one or more support protuberances responsive to being deflected toward the one or more support protuberances by flow of one or more of the first fluid or the second fluid into the at least one of the first check valve or the second check valve.

2. The infusion set check valve assembly of claim 1, wherein the first check valve and the second check valve prevent the first fluid from backflowing into the second inlet channel and prevent the second fluid from backflowing into the first inlet channel responsive to a blockage occurring in the patient line.

3. The infusion set check valve assembly of claim 1, wherein the second inlet port includes one or more of a connector configured to mate with a complementary connector fluidly coupled with the second container or a membrane configured to permit passage therethrough of a syringe needle to receive the second fluid.

4. The infusion set check valve assembly of claim 1, wherein the first inlet port, the second inlet port, and the outlet port are closer to each other within the self-contained housing than the first inlet port is to the first container along a first line that connects the first inlet port to the first container, closer to each other than the second inlet port is to the second container along a second line that connects the second inlet port to the second container, and closer to each other than the outlet port is to a patient along the patient line that connects the outlet port to the patient.

5. The infusion set check valve assembly of claim 1, wherein the first check valve is configured to open responsive to receiving the first fluid from a gravity feed set that includes the first container.

6. The infusion set check valve assembly of claim 1, wherein the self-contained housing has a Y-shape.

7. The infusion set check valve assembly of claim 1, wherein the outlet channel is configured to be connected to the patient line during infusion of fluids in the first container and the second container to a patient via the patient line, wherein the first check valve prevents backflow from the patient line into the first container and the second check valve prevents the backflow from the patient line into the second container.

8. The infusion set check valve assembly of claim 1, wherein the self-contained housing is configured to be disposed at a distal end or a proximal end of an intravenous (IV) set.

9. An infusion set fluid delivery system comprising:
a first container that retains a first fluid; and
an infusion set check valve assembly that includes a self-contained housing defining at least a first inlet port, a second inlet port, and a fluid outlet port, the first inlet port defining a first inlet channel through which the first fluid is received from the first container, the second inlet port defining a second inlet channel through which a second fluid is received from a second container that retains the second fluid, the outlet port defining an outlet channel through which one or more of the first fluid or the second fluid received into the self-contained housing via one or more of the first inlet port or the second inlet port is directed to a patient line, the infusion set check valve assembly also including a first check valve disposed within the self-contained housing between the outlet channel and the first inlet channel and a second check valve disposed within the self-contained housing between the outlet channel and the second inlet channel, wherein the first check valve controls flow of the first fluid from the first inlet channel to the patient line via the outlet channel and the second check valve controls flow of the second fluid from the second inlet channel to the patient line via the outlet channel, wherein the first check valve closes and blocks flow of the first fluid from the first inlet channel to the patient line via the outlet channel and the second check valve closes and blocks flow of the second fluid from the second inlet channel to the patient line via the outlet channel, wherein each of the first check valve and the second check valve includes a diaphragm, a restraining protuberance, and one or more support protuberances, the restraining protuberance abutting a center of the diaphragm, the one or more support protuberances disposed radially outward of the restraining protuberance, the restraining protuberance being longer than the one or more support protuberances, wherein the one or more support protuberances are sized to limit deflection of an outer annular portion of the diaphragm in that the outer annular portion of the diaphragm contacts the one or more support protuberances responsive to being deflected toward the one or more support protuberances by flow of one or more of the first fluid or the second fluid into the at least one of the first check valve or the second check valve.

10. The infusion set fluid delivery system of claim 9, wherein the first check valve and the second check valve prevent the first fluid from backflowing into the second inlet channel and prevent the second fluid from backflowing into the first inlet channel responsive to a blockage occurring in the patient line.

11. The infusion set fluid delivery system of claim 9, wherein the second inlet port includes one or more of a connector configured to mate with a complementary connector fluidly coupled with the second container or a membrane configured to permit passage therethrough of a syringe needle to receive the second fluid.

12. The infusion set fluid delivery system of claim 9, wherein the first inlet port, the second inlet port, and the outlet port are closer to each other within the self-contained housing than the first inlet port is to the first container along a first line that connects the first inlet port to the first container, closer to each other than the second inlet port is to the second container along a second line that connects the second inlet port to the second container, and closer to each other than the outlet port is to a patient along the patient line that connects the outlet port to the patient.

13. The infusion set fluid delivery system of claim 9, wherein the first check valve is configured to open responsive to receiving the first fluid from a gravity feed set that includes the first container.

14. The infusion set fluid delivery system of claim 9, wherein the self-contained housing has a Y-shape.

15. An infusion set check valve assembly comprising:
a self-contained housing that defines at least a first inlet port, a second inlet port, and a fluid outlet port, the first inlet port defining a first inlet channel through which a first fluid is received from a first container that retains the first fluid, the second inlet port defining a second inlet channel through which a second fluid is received from a second container that retains the second fluid, the outlet port defining an outlet channel through which one or more of the first fluid or the second fluid received into the self-contained housing via one or more of the first inlet port or the second inlet port is directed to a patient line;

a first check valve located between the first inlet channel and the outlet channel; and a second check valve located between the second inlet channel and the outlet channel, wherein the first check valve opens and permits flow of the first fluid from the first inlet channel to the patient line via the outlet channel, the second check valve opens and permits flow from the second inlet channel to the patient line via the outlet channel, wherein the first check valve closes and prevents flow of the first fluid from the first inlet channel to the patient line via the outlet channel while the second check valve remains open and permits continued flow of the second fluid from the second inlet channel to the patient line via the outlet channel, wherein each of the first check valve and the second check valve includes a diaphragm, a restraining protuberance, and one or more support protuberances, the restraining protuberance abutting a center of the diaphragm, the one or more support protuberances disposed radially outward of the restraining protuberance, the restraining protuberance being longer than the one or more support protuberances, wherein the one or more support protuberances are sized to limit deflection of an outer annular portion of the diaphragm in that the outer annular portion of the diaphragm contacts the one or more support protuberances responsive to being deflected toward the one or more support protuberances by flow of one or more of the first fluid or the second fluid into the at least one of the first check valve or the second check valve.

16. The infusion set check valve assembly of claim 15, wherein the first check valve and the second check valve prevent the first fluid from backflowing into the second inlet channel and prevent the second fluid from backflowing into the first inlet channel responsive to a blockage occurring in the patient line.

* * * * *